(12) United States Patent
Duffield et al.

(10) Patent No.: US 9,925,064 B2
(45) Date of Patent: *Mar. 27, 2018

(54) INTERVERTEBRAL FUSION IMPLANT

(71) Applicant: GLOBUS MEDICAL, INC., Audubon, PA (US)

(72) Inventors: William E. Duffield, Collegeville, PA (US); Colm McLaughlin, Glenside, PA (US); Jason Gray, East Greenville, PA (US); Jamie Carroll, Drexel Hill, PA (US); Mark Adams, Downingtown, PA (US); William S. Rhoda, Media, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/442,134

(22) Filed: Feb. 24, 2017

(65) Prior Publication Data

US 2017/0156883 A1   Jun. 8, 2017

Related U.S. Application Data

(63) Continuation of application No. 14/209,504, filed on Mar. 13, 2014, now Pat. No. 9,615,936, which is a continuation of application No. 12/477,958, filed on Jun. 4, 2009, now Pat. No. 8,709,083.

(51) Int. Cl.
*A61F 2/44* (2006.01)
*A61F 2/30* (2006.01)
*A61F 2/46* (2006.01)

(52) U.S. Cl.
CPC .......... *A61F 2/447* (2013.01); *A61F 2/30771* (2013.01); *A61F 2/4465* (2013.01); *A61F 2/4684* (2013.01); *A61F 2002/3082* (2013.01); *A61F 2002/30403* (2013.01); *A61F 2002/30433* (2013.01); *A61F 2002/30436* (2013.01); *A61F 2002/30492* (2013.01); *A61F 2002/30509* (2013.01); *A61F 2002/30517* (2013.01); *A61F 2002/30578* (2013.01); *A61F 2002/30787* (2013.01); *A61F 2002/30794* (2013.01); *A61F 2002/30843* (2013.01); *A61F 2002/30904* (2013.01); *A61F 2002/4475* (2013.01); *A61F 2310/00023* (2013.01)

(58) Field of Classification Search
CPC .......... A61F 2/44; A61F 2/4455; A61F 2/447
See application file for complete search history.

*Primary Examiner* — Nicholas Woodall

(57) ABSTRACT

The present invention provides an intervertebral implant for implantation in a treated area of an intervertebral space between vertebral bodies of a spine. The implant includes a spacer portion having an inferior and superior surface, wherein the inferior and superior surfaces each have a contact area capable of engaging with anatomy in the treated area, and the inferior and superior surfaces define a through-hole extending through the spacer body. The present invention further provides screw holes extending from a side portion to the inferior and superior surfaces of the spacer portion and a plate portion coupled to the spacer portion through a coupling means, wherein the plate portion contains screws holes for receiving screws. A screw back out prevention mechanism adapted on the plate portion and prevents the back out of screws from the screw holes.

20 Claims, 6 Drawing Sheets

INTERVERTEBRAL FUSION IMPLANT

CROSS-REFERENCE TO RELATED APPLICATIONS

The present application is a continuation of U.S. application Ser. No. 14/209,504, which is a continuation of U.S. application Ser. No. 12/477,958, filed on Jun. 4, 2009, now issued as U.S. Pat. No. 8,709,083, which are each incorporated by reference herein in their entirety.

FIELD OF THE INVENTION

The present disclosure generally relates to a fixation device for positioning and immobilizing at least two adjacent vertebra. In particular, the present invention relates to a stand alone interbody fusion device for implementation in the spine.

BACKGROUND OF THE INVENTION

The vertebrate spine is the axis of the skeleton on which all of the body parts "hang". In humans, the normal spine has seven cervical, twelve thoracic and five lumbar segments. The lumbar spine situs upon the sacrum, which then attaches to the pelvis, and in turn is supported by the hip and leg bones. The bony vertebral bodies of the spine are separated by intervertebral discs, which act as joints but allow known degrees of flexion, extension, lateral bending, and axial rotation.

The typical vertebra has a thick anterior bone mass called the vertebral body, with a neural (vertebral) arch that arises from the posterior surface of the vertebral body. The central of adjacent vertebrae are supported by intervertebral discs. The spinal disc and/or vertebral bodies may be displaced or damaged due to trauma, disease, degenerative defects, or wear over an extended period of time. One result of this displacement or damage to a spinal disc or vertebral body may be chronic back pain. In many cases, to alleviate back pain from degenerated of herniated discs, the disc is removed along with all or part of at least one neighboring vertebrae and is replaced by an implant that promotes fusion of the remaining bony anatomy.

However, the success or failure of spinal fusion may depend upon several factors. For instance the spacer or implant or cage used to fill the space left by the removed disc and bony anatomy must be sufficiently strong to support the spine under a wide range of loading conditions. The spacer should also be configured so that it likely to remain in place once it has been positioned in the spine by the surgeon. Additionally the material used for the spacer should be biocompatible material and should have a configured that promotes bony ingrowth.

In combination with spacers or cages, a plating system is used to further stabilize the spine during the fusion process. These devices, commonly referred to as bone fixation plating systems, typically include one or more plates and screws for aligning and holding vertebrae in a fixed position with respect to one another. Plating systems independent of the spacers provide additional complications such as loosening and failure of the hardware. Two common failures are the breakage of the plates, and the backing out of screws into soft tissues of the patient's body. The backing out of the screws is typically a result of the screws failure to achieve a sufficient purchase in the bone, although the stripping of the screws has also been known to cause this problem.

There is a need for a spine stabilization system that in promotes fusion of adjacent vertebrae while at the same time provides stabilization of the spinal area where fusion occurs. There is a need for a system that incorporates both the fusion element and the plating element in one system to reduce the possible complications that may occur. There is also a need to provide a system that reduces the complications that may occur in the fusion element and the plating element and to need for this system to be configured so that positioning this system is efficient and easy.

SUMMARY OF THE INVENTION

The present invention provides an intervertebral implant for implantation in a treated area of an intervertebral space between vertebral bodies of a spine. The implant includes a spacer portion having an inferior and superior surface, wherein the inferior and superior surfaces each have a contact area capable of engaging with anatomy in the treated area, and the inferior and superior surfaces define a through-hole extending through the spacer body. The present invention further provides screw holes extending from a side portion to the inferior and superior surfaces of the spacer portion and a plate portion coupled to the spacer portion through a coupling means, wherein the plate portion contains screws holes for receiving screws. A screw back out prevention mechanism adapted on the plate portion and prevents the back out of screws from the screw holes.

DETAILED DESCRIPTION OF THE ILLUSTRATED EMBODIMENTS

Figure 3:
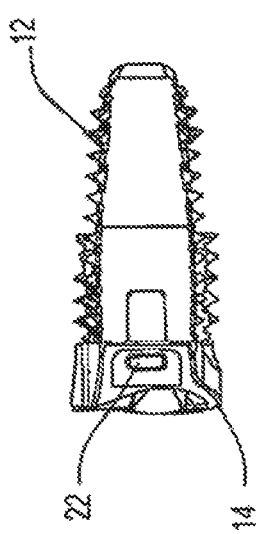
FIG. 3 is a side view of the intervertebral implant of FIG. 1.
Figure 4:
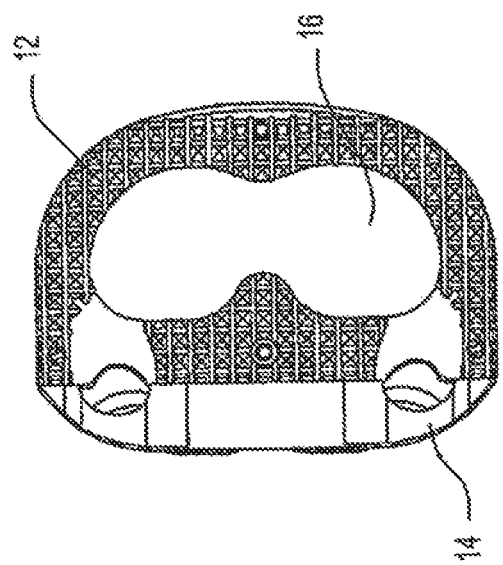
FIG. 4 is a top view of the intervertebral implant of FIG. 1.

Embodiments of the disclosure are generally directed to flexible stabilization systems for use with the anterior, antero-lateral, lateral, and/or posterior portions of at least one motion segment unit of the spine. The systems of the invention are designed to be conformable to the spinal anatomy, so as to be generally less intrusive to surrounding tissue and vasculature than existing rigid stabilization systems.

Certain embodiments may be used on the cervical, thoracic, lumbar, and/or sacral segments of the spine. For example, the size and mass increase of the vertebrae in the spine from the cervical to the lumbar portions is directly related to an increased capacity for supporting larger loads. This increase in load bearing capacity, however, is paralleled by a decrease in flexibility and an increase in susceptibility to strain. When rigid immobilization systems are used in the lumbar segment, the flexibility is decreased even further beyond the natural motion restriction of that segment. Replacing the conventional rigid immobilization systems with certain embodiments disclosed herein may generally restore a more natural movement and provide added support to the strain-susceptible area.

FIGS. 1-8 illustrate the different views of one particular embodiment of the present invention. The intervertebral fusion implant as shown in FIGS. 1-8 is a stand-alone anterior lumbar interbody fusion device used to provide structural stability in skeletally mature individuals following discectomies. These implants are available in various heights and geometric options to fit the anatomically needs of a wide variety of patients.

Specifically, FIGS. 1-4 illustrate one embodiment of an intervertebral fusion implant 10 according to the present invention. Implant 10 is generally positioned in the intervertebral space between two adjacent vertebrae. As shown in the figures, implant 10 primarily incorporates a spacer portion 12 and a plate portion 14. In this particular embodiment, the spacer portion 12 includes a graft window 16 for the placement of bone graft to enhance fusion between two adjacent vertebrae. The plate portion 14 includes at least one screw hole 18, however, in the preferred embodiment of the present invention, three screw holes 18 are provided. Also, in the plate portion 14 of the implant 10, a screw back out prevention mechanism 20 is provided. There is also provided a coupling means 22 which connect the spacer portion 12 and the plate portion 14 rigidly to each other. The coupling means 22 will be discussed in greater detail with reference to FIGS. 5-8.

The spacer portion 12 can be comprised of any material that is conducive to the enhancement of fusion between the two adjacent vertebrae. In one particular embodiment, the spacer portion 12 is made of PEEK material which is physiologically compatible. It should be noted that any other material that are physiologically compatible may also be used. The spacer portion 12 is made from radiolucent polymer in order to permit radiographic visualization. The spacer portion 12 further comprises superior and inferior portions that are provided with a plurality of pyramidal protrusions 13. The superior and inferior portions of the spacer portion are bi-convex for greater contact with the vertebral endplates of the adjacent vertebrae. The protrusions 13 can be configured to be any size or shape for further anchoring the spacer portion 12 to each of the adjacent vertebrae. Protrusions 13 on the superior and inferior surfaces of each implant grip the endplates of the adjacent vertebrae to aid in expulsion resistance.

Figure 1:
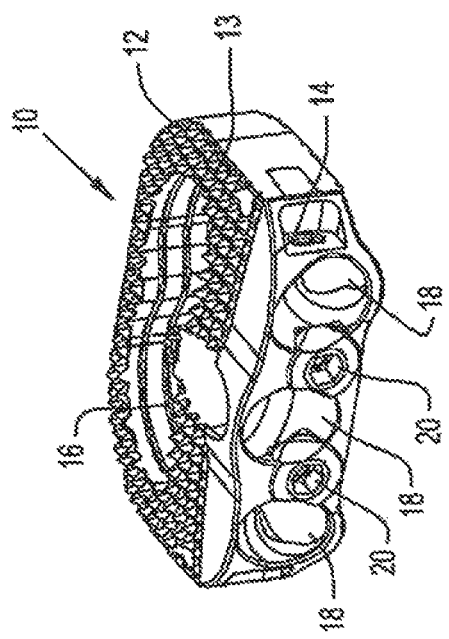
FIG. 1 is a perspective view of one embodiment of an intervertebral implant according to the present invention.
Figure 2:
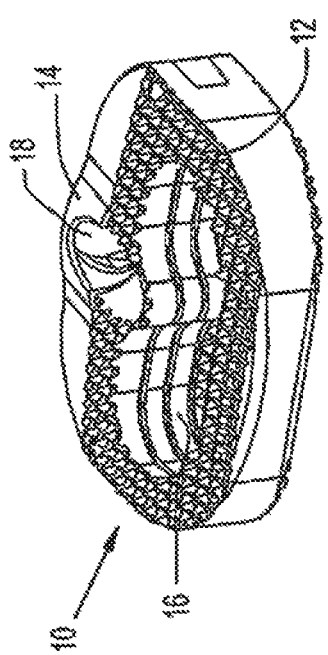
FIG. 2 is another perspective view of the embodiment of the implant shown in FIG. 1.

The plate portion 14 can also be comprised of any physiologically compatible material. In the preferred embodiment, the plate portion of the implant 10 is composed of titanium. The plate portion 14 as illustrated in FIG. 1, are provided with three screw holes. However, it should be noted that implant 10 may be comprised of only one screw hole. The screw holes 18 are situated both in the spacer portion 12 and the plate portion 14 for receiving bone screws which are attached to the adjacent vertebral bodies at different angles.

Figure 5:
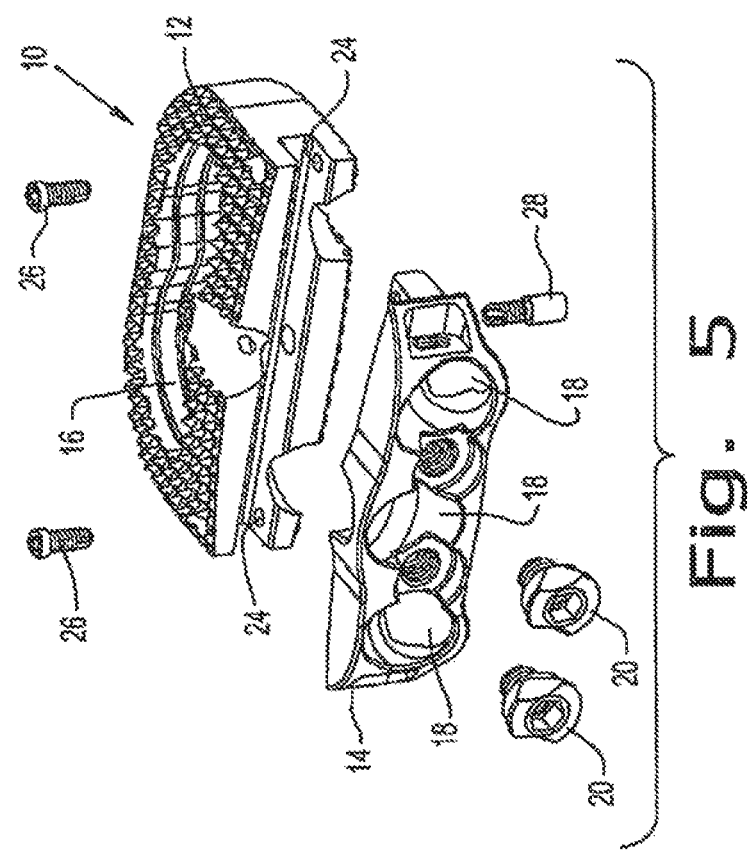
FIG. 5 is an exploded view of the intervertebral implant of FIG. 1.

FIG. 5 illustrates an exploded view of the intervertebral stand along fusion device 10. In this exploded view, clearer view of the combination of the plate portion 14 and the spacer portion 12 is illustrated. The spacer portion 12 and the plate portion 14 are coupled to each other view connection points 24 and through the use of connection pins 26 and 28.

Figure 6:
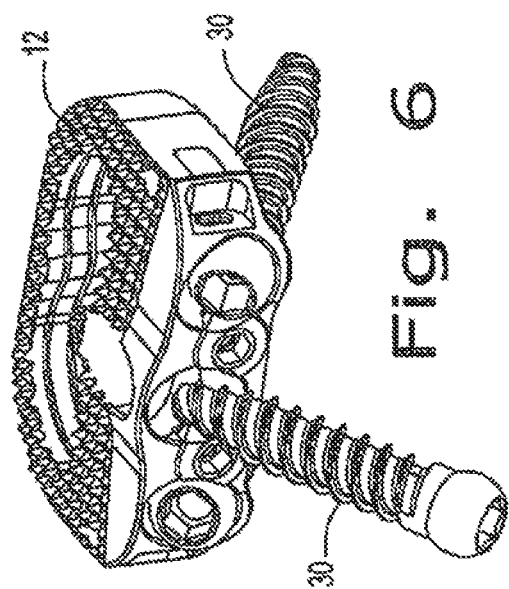
FIGS. 6 and 7 is a perspective view of the intervertebral implant of FIG. 1 which include illustrations of bone fasteners.
Figure 7:
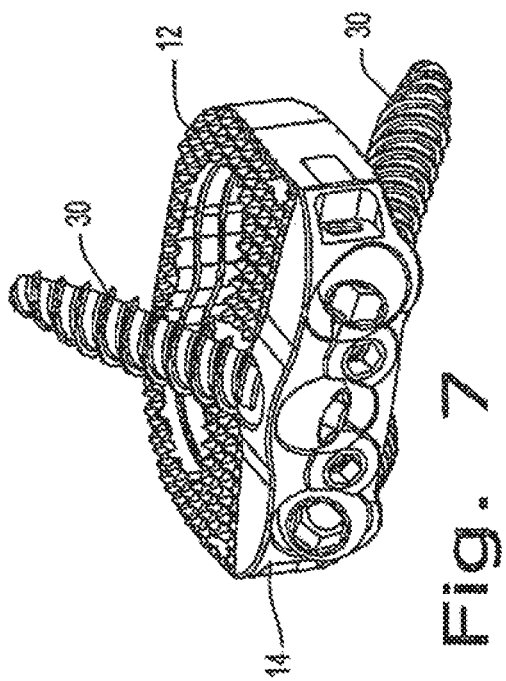
Figure 8:
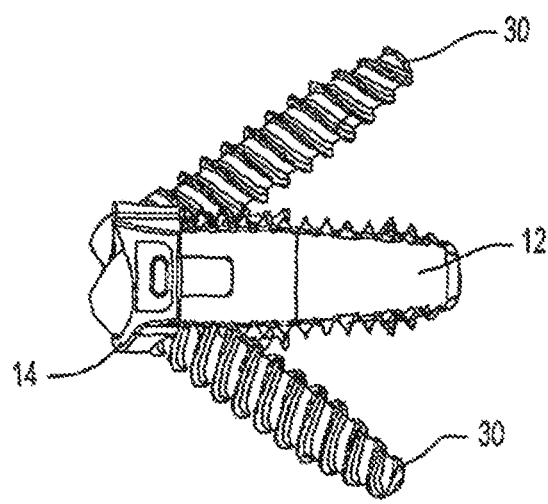
FIG. 8 is another side view of the intervertebral implant of FIG. 1 incorporating bone fasteners.

FIGS. 6-8 illustrate the fusion device 10 in various views associated with the screws 30 provided in pin holes 18. The pin holes 18 are configured to receive screws 30 at various angles. The screws 30 enter the pin holes at specified angles to enter the adjacent vertebral bodies at the optimal locations. The screws 30 are configured and adapted to provide optical purchase with the adjacent vertebral bodies.

Now, turning to the method of positioning the implant, it should be noted that the intervertebral implant 10 is positioned in the spine after the disc portion between two vertebral bodies is exposed and removed using rongeurs and other suitable instruments. The posterior and lateral walls of the annulus are generally preserved to provide peripheral support for the implant and graft materials. A trial device attached to a trial holder is then inserted into the disc space to determine size of the implant. This procedure is generally conducted using fluoroscopy and tactile feel. After the appropriate sized implant is selected and attached to an implant holder and drill guide, the implant may be inserted into the disc space. Once the implant is positioned with the disc space, supplemental graft material can used to enhance fusion. Once the implant is positioned inside the disc, an awl or any similar type of instrument can be used to drill through the screw hole and break the cortex of the adjacent vertebral body. The surgeon performing this procedure may then use a depth gauge to determine the screw length. Once the appropriate screw length is determined, screws are inserted using a self-retaining screwdriver. After the screws are finally inserted and secure thereby providing solid purchase with the adjacent vertebral bodies, the screw anti back out mechanism is engaged and secure. In this particular embodiment, the anti back out mechanism is two set screws that retain the three screws with the implant.

Figure 9:
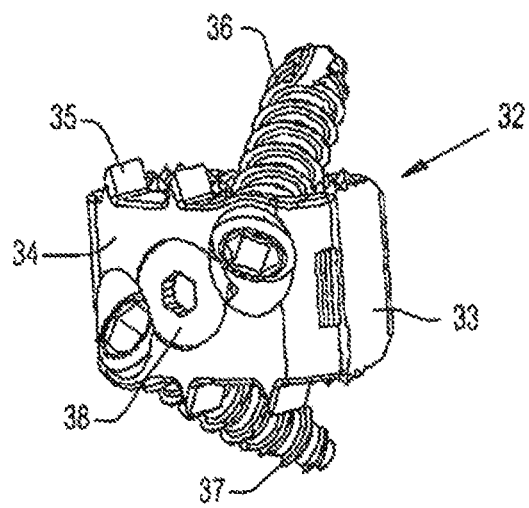
FIG. 9 is a perspective view of another embodiment of the stand alone intervertebral implant.

FIG. 9 illustrates a perspective view of the stand alone intervertebral implant 32 for positioning in the cervical region of the spine. The present invention relates to an implant having a peek spacer portion 33 that is coupled to a titanium plate portion 34 through the use of titanium dowel pins. However, it should be noted that the titanium plate portion 34 and the peek spacer portion 33 maybe coupled through any other feasible means such as hooks, screws, and any other type of fastening means. The implant 32 also allows for at least two titanium screws 36 and 37 to be inserted at a compound angle for maximum screw purchase into the superior and inferior vertebral bodies. A locking mechanism 38 is provided on the plate portion 34 to capture the sides of both of the at least two screws 36 and 37 with a 90 degree turn preventing the titanium screws 36 and 37 from backing out. It should be noted that the present application is not limited to being of a PEEK spacer and a titanium plate. Other materials that are physiologically compatible which are similar and which may be unique to spacers and plates may be utilized in various combinations.

Figure 10:
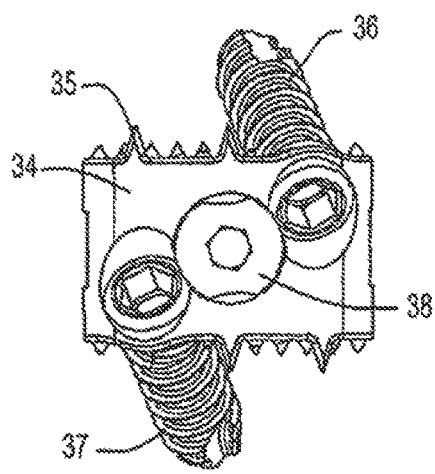
FIG. 10 is a front view of the intervertebral implant of FIG. 9.
Figure 11:
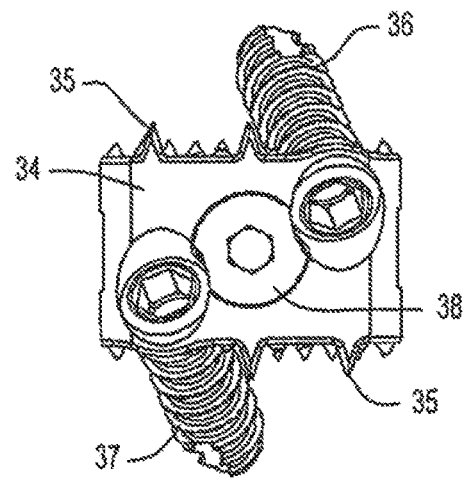
FIG. 11 is a top view of the stand alone intervertebral implant illustrated in FIG. 9.

FIGS. 10 and 11 illustrate the front view of the plate portion of the implant. Specifically, FIGS. 10 and 11 illustrate an open and a close position with reference to the anti back out mechanism 38. Also, it should be noted that the titanium plate 34 is provided with knife like edges 35 which are designed to engage the vertebral body and provides additional torsional stability to that of the bone screws. The plate 35 is also provided with "eye brows" like structure which fully captures the bone screws 36 and 37 while still allowing for the screws to reside about the tooth root plane and remaining lower than the tooth (protrusions on the spacer portion 33). The plate 35 geometry allows for the minimum reduction of peek volume. The plate 35 height remains level to the peek tooth root so that compressive loads are always subjected to the peek body where the graft is contained. Compound holes are drilled to accept bone screws 36 and 37 and to allow for fixed or variable angle screws. The anti back out mechanism is engaged so that the screws 26 and 37 do not back out of the implant 32.

Figure 12:
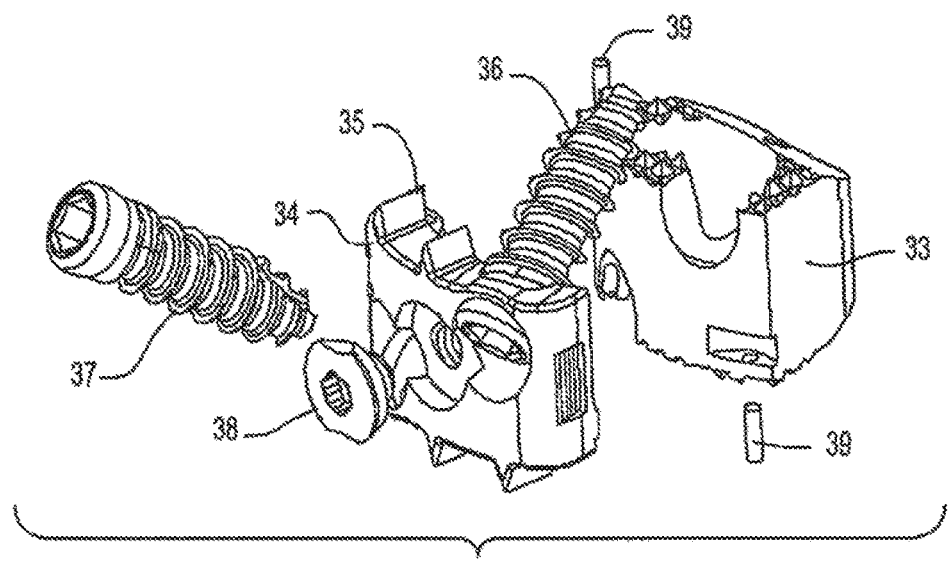
FIG. 12 is an exploded view of the stand alone intervertebral implant of FIG. 9.
Figure 14:
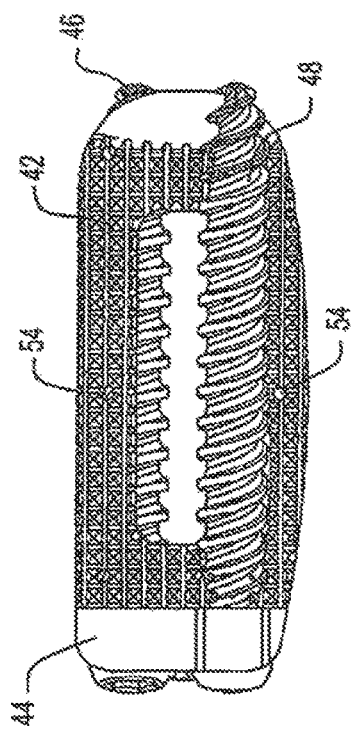
FIG. 14-16 are different views of the stand alone intervertebral implant of FIG. 13.
Figure 16:
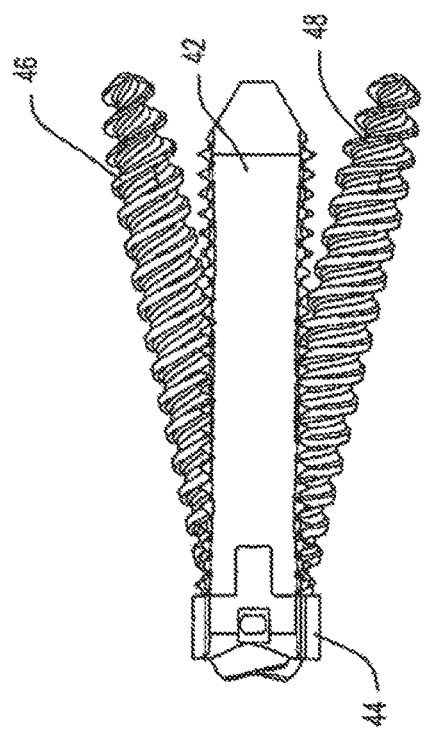
Figure 13:
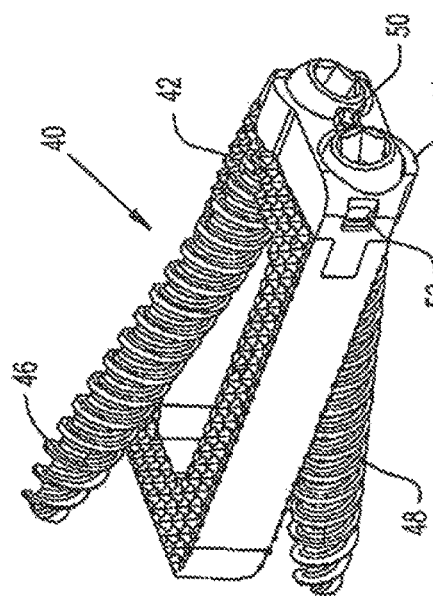
FIG. 13 is yet another embodiment of the stand alone intervertebral implant.
Figure 15:
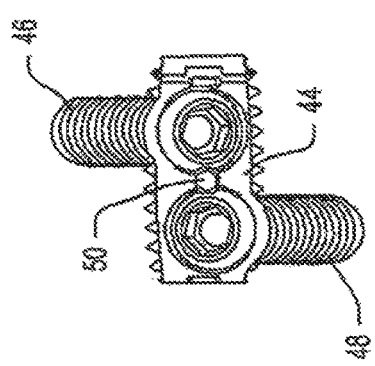

FIG. 12 illustrates an exploded view of the intervertebral implant. The plate portion 34 and spacer portion 33 have at least 2 male and female ledges which are capable of interfacing with each other. The connection of the male and female ledges are offset at different heights to minimize cross-sectional area loss. Also illustrated in FIG. 12 is the dowel pins used to connect the spacer portion to the plate portion as one means of coupling of the spacer portion 33 and the plate portion 34. It should be noted that various means such as hooks, staples and screws can be used to attach the spacer portion to the plate portion of the present invention.

The spacer portion 33 of the implant provides a leading edge chamfer which enables self distraction of the vertebral bodies while inserting. The spacer portion 33 also provides teeth like structures in the superior and inferior aspects of the spacer body to help prevent migration of the implant. The root of the teeth or protrusions on the base of the implant serves as the defining plane for the superior and inferior vertebral bodies. Finally, the spacer portion 33 provides an axial shaped hole which enables a maximum amount of graft for packing within the implant. However, it should be noted that the graft hole can be designed to be multiple holes or any in other geometrical shape to enhance fusion through the insertion of graft material.

FIGS. 13-16 illustrate a stand-alone fusion device for position in a lateral approach. The stand-alone fusion device 40 consists of a spacer portion 42 and a plate potion 44. The spacer portion and the plate portion are configured to be able to receive screws 46 and 48 for attachment to adjacent vertebral bodies. The plate portion 44 is provided with an anti back out mechanism 50 so that the screws 46 and 48 are fixedly retained within the fusion device 40.

Figure 17:
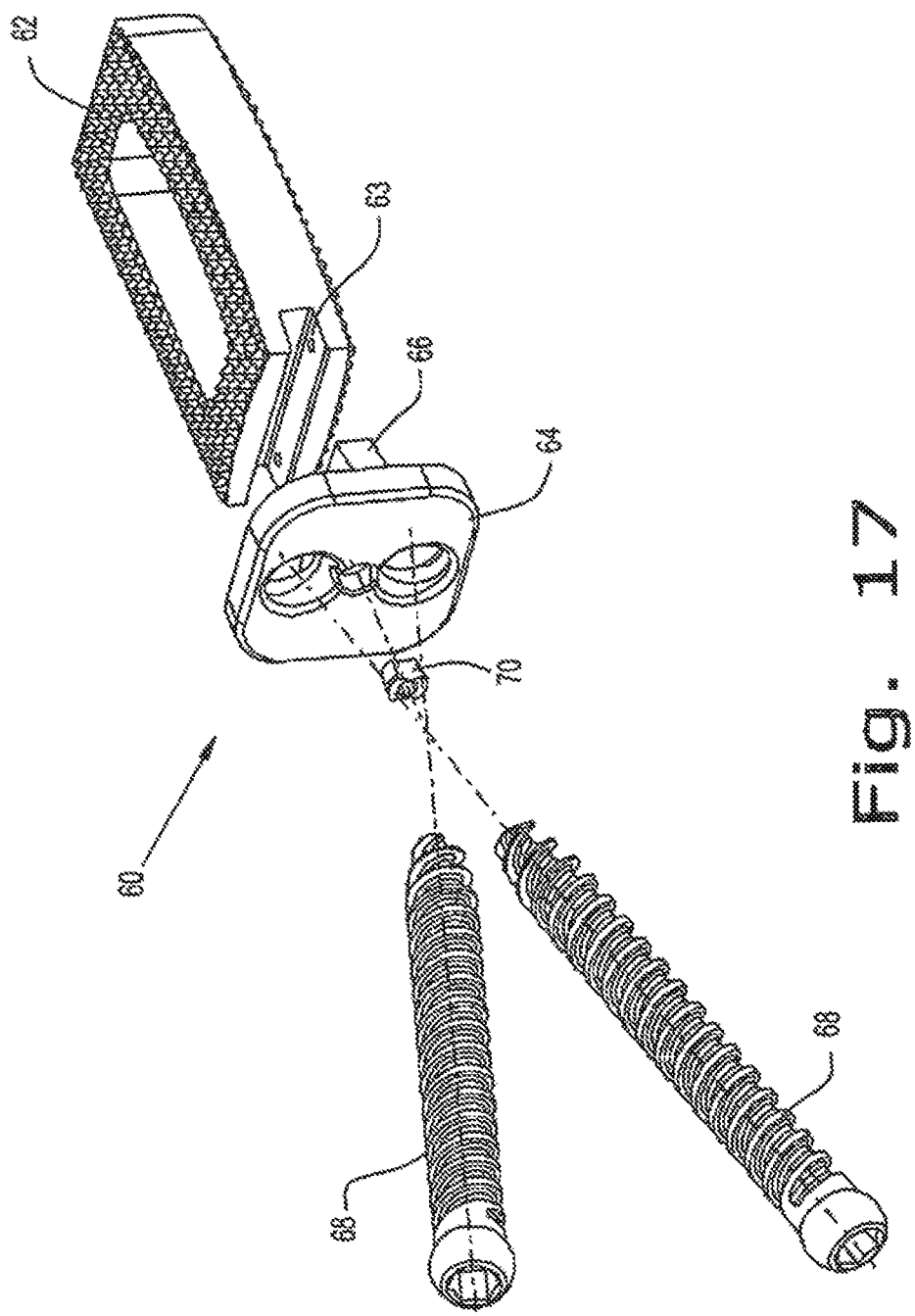
FIG. 17 is another embodiment of the implant of FIG. 14 according to the present invention.

FIG. 17 illustrates another embodiment of a stand-alone intervertebral implant 60 that is poisoned into the disc space laterally. In this embodiment, which is similar to the embodiment disclosed in FIGS. 13-16, the spacer portion 62 is provided with a plurality of protrusions in the superior and inferior portions. These protrusions grip the endplates of the adjacent vertebrae to aid in expulsion resistance. The spacer portion 62 also contains a plate receiving area 63 for receiving the plate portion 64. The plate receiving area 62 is configured to receive a plate protrusion 66 for coupling the spacer portion 62 and the plate portion 63 together through the use of pins or any other similar type of coupling means.

The plate portion 64 is configured with at least two screw holes for receiving screws 68. The screws 68 are positioned at angles to insert through the spacer and the adjacent vertebral body to gain maximum purchase and stability. The screws 68 are retained with the implant 60 through the use of an anti screw back out mechanism 70. When this mechanism is engaged by turning at least 90 degrees through the use an instrument such as a screwdriver, the screws 68 are maintained within the implant and the boney structure of the adjacent vertebral bodies.

While it is apparent that the invention disclosed herein is well calculated to fulfill the objects stated above, it will be appreciated that numerous modifications and embodiments may be devised by those skilled in the art.

What is claimed is:

1. An intervertebral implant for implantation in a treated area of an intervertebral space between vertebral bodies of a spine, wherein said implant comprises:

a spacer having, an inferior and superior surface, wherein the inferior and superior surfaces each have a contact area capable of engaging with anatomy in the treated area, and the inferior and superior surfaces define a through-hole having an inner surface extending through the spacer; and a plate rigidly coupled to the spacer, wherein the plate contains screw holes for receiving fasteners, wherein a fastener back out prevention mechanism is adapted on the plate for preventing the back out of screws from the screw holes, wherein the plate comprises at least one extension that is adapted to mate with at least one connection groove on an anterior portion of the spacer, wherein the at least one connection groove in the spacer includes a first vertical opening for receiving a first connection pin therethrough and a second vertical opening for receiving a second connection pin therethrough to thereby secure the plate to the spacer, wherein the fastener back out prevention mechanism includes a rotatable element that in a first position allows for at least two fasteners to be inserted or removed from the screw holes of the plate and when rotated into a second position secures the at least two fasteners within the intervertebral implant, and wherein the plate is not moveable with respect to the spacer.

2. The intervertebral implant of claim 1, wherein the at least two fasteners are configured to be inserted into adjacent vertebral bodies at divergent angles.

3. The intervertebral implant of claim 1, wherein first connection pin and the second connection pin rigidly couple the spacer with the plate.

4. The intervertebral implant of claim 1, wherein the plate and the spacer are configured to structurally mate with one another.

5. The intervertebral implant of claim 1, wherein the plate is comprised of metal.

6. The intervertebral implant of claim 1, wherein at least one groove is configured circumferentially on the inner surface of the spacer.

7. The intervertebral implant of claim 1, wherein the spacer is comprised of plastic.

8. The intervertebral implant of claim 1, wherein the spacer comprises a plurality of protrusions on superior and inferior surfaces of the spacer.

9. An intervertebral implant for implantation in a treated area of an intervertebral space between vertebral bodies of a spine, wherein said implant comprises:

a spacer having an inferior and superior surface, wherein the inferior and superior surfaces each have a contact area capable of engaging with anatomy in the treated area, and the inferior and superior surfaces define a through-hole and an inner surface extending through the spacer;

a plate rigidly coupled to the spacer, wherein the plate contains screws holes for receiving screws; and a screw back out prevention mechanism adapted on the plate that prevents the back out of screws from the screw holes, wherein the plate comprises at least one extension that is adapted to mate with at least one connection groove on an anterior portion of the spacer, wherein the at least one connection groove in the spacer includes a first vertical opening for receiving a first connection pin therethrough and a second vertical opening for receiving a second connection pin therethrough to thereby secure the plate to the spacer, wherein the fastener back out prevention mechanism includes a rotatable element that in a first position allows for at least two fasteners to be inserted or removed from through holes of the plate and when rotated into a second position secures the at least two fasteners within the intervertebral implant.

10. The intervertebral implant of claim 9, wherein the at least two fasteners are configured to be inserted into adjacent vertebral bodies at divergent angles.

11. The intervertebral implant of claim 9, wherein at least one pin couples the spacer portion and the plate of the intervertebral implant.

12. The intervertebral implant of claim 9, wherein the plate and the spacer are configured to structurally mate with one another.

13. The intervertebral implant of claim 9, wherein the plate is comprised of metal and the spacer is comprised of plastic.

14. The intervertebral implant of claim 9, wherein the spacer comprises a plurality of protrusions on the superior and inferior surfaces of the spacer.

15. An implant for positioning between adjacent intervertebral bodies comprising:

a spacer having an anterior portion, a posterior portion, first and second side portions, and superior and inferior surfaces; and a plate having an anterior face and a posterior face, first and second side portions, and superior and inferior surfaces, wherein the plate comprises at least one extension extending out from a posterior portion of the plate, wherein the at least one extension of the plate mates with at least one connection groove of the spacer, the at least one connection groove of the spacer configured on the anterior portion of the spacer, wherein the at least one connection groove in the spacer includes a first opening for receiving a first connection pin therethrough and a second opening for receiving a second connection pin therethrough to thereby secure the plate to the spacer, wherein the first connection pin and the second connection pin couple the spacer to the plate so that the plate does not move with respect to the spacer, wherein the fastener back out prevention mechanism includes a rotatable element that in a first position allows for at least two fasteners to be inserted or removed from through holes of the plate and when rotated into a second position secures the at least two fasteners within the intervertebral implant.

16. The intervertebral implant of claim 15, wherein the at least two fasteners are configured to be inserted into adjacent vertebral bodies at divergent angles.

17. The intervertebral implant of claim 15, wherein the first connection pin is received vertically through the first opening and the second connection pin is received vertically though the second opening.

18. The intervertebral implant of claim 15, wherein the plate and the spacer are configured to structurally mate with one another.

19. The intervertebral implant of claim 15, wherein the plate is comprised of metal and the spacer is comprised of plastic.

20. The intervertebral implant of claim 15, wherein the spacer comprises a plurality of protrusions on the superior and inferior surfaces of the spacer.

\* \* \* \* \*